United States Patent [19]

Voelkel

[11] Patent Number: 5,160,312
[45] Date of Patent: Nov. 3, 1992

[54] CRYOPRESERVATION PROCESS FOR DIRECT TRANSFER OF EMBRYOS

[75] Inventor: Steven A. Voelkel, Bryan, Tex.

[73] Assignee: W. R. Grace & Co.-Conn., New York, N.Y.

[21] Appl. No.: 651,458

[22] Filed: Feb. 6, 1991

Related U.S. Application Data

[63] Continuation-in-part of Ser. No. 478,216, Feb. 9, 1990, abandoned.

[51] Int. Cl.$^5$ .............................................. A61B 17/43
[52] U.S. Cl. ...................................................... 600/34
[58] Field of Search ........................................... 600/34

[56] References Cited

U.S. PATENT DOCUMENTS

| | | | |
|---|---|---|---|
| 4,380,997 | 4/1983 | Leibo | 128/1 R |
| 4,512,337 | 4/1985 | Leveskis | 600/34 |

FOREIGN PATENT DOCUMENTS 8809816 12/1988 PCT Int'l Appl. .
8907135 8/1989 PCT Int'l Appl. .

OTHER PUBLICATIONS

Bondioli, et al, "The Effect of Trypsin Washing on Post Thaw Viability of Bovine Embryos", Proceedings of the 7th Annual Convention, American Embryo Transfer Association (1988).
Bui-Xuan-Nguyen, et al., "Direct Freezing of Cattle Embryos After Partial Dehydration at Room Temperature", *Theriogenology*, vol. 22, pp. 389-399 (1984).
Chupin, et al., "Comparison of Two Methods for One-Step In-Straw Thawing and Direct Transfer of Cattle Blastocysts", *Theriogenology*, vol. 21, pp. 455-459 (1984).
Echternkamp, et al., "Exposure of Bovine Embryos to Trypsin During Washing Does Not Decrease Embryonic Survival", *Theriogenology*, vol. 29, pp. 131-137 (1989).
Heyman, et al., "Transfer of Frozen-Thawed Embryos in Sheep", *Veterinary Record* vol. 120, pp. 83-85 (1987).
Leibo, "A One-Step Method for Direct Nonsurgical Transfer of Frozen-Thawed Bovine Embryos", *Theriogenology*, vol. 21, pp. 767-790 (1984).
Massip & van der Zwalmen, "Direct Transfer of Frozen Cow Embryos in Glycerol-Sucrose", *Veterinary Record*, vol. 115, pp. 327-328 (1984).
Massip, et al., "Recent Progress in Cryopreservation of Cattle Embryos", *Theriogenology*, vol. 27, pp. 69-79 (1987).
Miyamoto & Ishibashi, "Survival of Frozen-Thawed Mouse and Rat Embryos in the Presence of Ethylene Glycol", *J. Reprod. Fert.*, vol. 54, pp. 427-432 (1978).
Miyamoto & Ishibashi, "The Protective Action of Glycols Against Freezing Damage of Mouse and Rat Embryos", *J. Reprod. Fert.*, vol. 54, pp. 427-432 (1978).
Renard, et al., "Cervical Transfer of Deep Frozen Cattle Embryos", *Theriogenology*, vol. 15, pp. 311-320 (1981).
Renard, et al., "Freezing Bovine Blastocysts with 1,2-Propanediol as Cryoprotectant", *Theriogenology*, vol. 15, p. 113 (1981).
Renard, et al., "Cervical Transfer of Deep Frozen Cattle Embroys: A New Procedure for One Step Thawing Inside French Straw", *Ann. Med. Vet.*, vol. 126, pp. 23-32 (1982).
Renard, et al., "Sucrose Dilution: A Technique for Field Transfer of Bovine Embryos Frozen in the Straw", *Theriogenology*, vol. 19, p. 145 (1983).

(List continued on next page.)

*Primary Examiner*—David Isabella
*Assistant Examiner*—Gina M. Gualtieri
*Attorney, Agent, or Firm*—Vanessa L. Appleby; Steven T. Trinker

[57] ABSTRACT

An improved cryopreservation of embryos has been developed. After freezing in a cryoprotective solution of ethylene glycol, glycerol or a combination thereof, the embryos can be thawed and transferred directly to the recipient animal without serial rehydration. The transfer can be made directly from the cryoprotective container to the recipient animal.

21 Claims, 2 Drawing Sheets

OTHER PUBLICATIONS

Suzuki, et al., "Comparison of One Step Sucrose Dilution and Direct Transfer of Frozen Bovine Embryos in Glycerol and 1,2-Propanediol", *Theriogenology*, vol. 33, p. 334 (1990).

Szell, et al., "Osmotic Characteristics of Sheep and Cattle Embryos", *Cryobiology*, vol. 26, pp. 297-301 (1989).

Hernandez-Ledezma, et al., "Freezing of Mouse Embryos with a Cryoprotectant Mixture (CPM) of Glycerol and 1,2-Propanediol", Theriogenology vol. 29, p. 258 (1988).

Hernandez-Ledezma, et al., "One Step Sucrose Dilution of a Cryoprotectant Mixture (CPM) of Glycerol and 1,2-Propanediol", *Theriogenology*, vol. 29, p. 258 (1988).

Edwards, "Maturation in Vitro of Mouse, Sheep, Cow, Pig, Rhesus Monkey and Human Ovarian Oocytes", *Nature*, vol. 208, pp. 349-351 (1965).

Lu, et al., "Pregnancy Established in Cattle by Transfer of Embryos Derived from in Vitro Fertilization of Oocytes Matured in Vitro", *Veterinary Record*, vol. 121, pp. 259-260 (1987).

Coon, "Clonal Culture of Differentiated Rat Liver Cells", 39 *J. Cell Biol.* 29a (1968).

"A Partially Purified Polypeptide Fraction from Rat Liver Cell Dulak & Temin, Conditioned Medium with Multiplication-Stimulating Activity for Embryo Fibroblasts", 81 *J. Cell Physiol.* 153-60 (1973).

Dulak & Temin, "Multiplication-Stimulating Activity for Chicken Embryo Fibroblasts from Rat Liver Cell Conditioned Medium: A Family of Small Polypeptides", 81 *J. Cell Physiol.* 161-70 (1973).

Marquardt & Todaro, "Purification and Primary Structure of a Polypeptide with Multiplication-Stimulating Activity from Rat Liver Cell Cultures", 256 *J. Biol. Chem.* 6859-65 (1981).

Moses et al., "Purification and Characterization of Multiplication-Stimulating Activity", 103 *Eur. J. Biochem.* 387-400 (1980).

Moses et al., "Immunological Cross-Reactivity of Multiplication-Stimulating Activity Polypeptides", 103 *Eur. J. Biochem.* 401-08 (1980).

Voelkel, "In Vitro Culture of Preimplantation Embryos", NIH Research Grant No. 1 R43 HD 24842-01, dated Jun. 14, 1989.

CRYOPRESERVATION PROCESS FOR DIRECT TRANSFER OF EMBRYOS

This patent application is a continuation-in-part of U.S. patent Ser. No. 478,216, filed Feb. 9, 1990, now abandoned entitled "Cryopreservation Process for Direct Transfer of Embryos", by Steven A. Voelkel, inventor.

TECHNICAL FIELD

The present invention is a process for cryopreservation of embryos. After thawing, the embryos can be transferred directly to recipient animals without special handling. The cryoprotectant can be ethylene glycol, glycerol, or any combination thereof. Another aspect of this invention involves pretreating the embryos with various detergents, organic solvents and proteolytic enzymes. In addition, trophoblastic tissues from other viable embryos can be processed with the embryos to enhance the results of the cryopreservation process.

BACKGROUND

Embryos in the morula or blastocyst stage can be frozen in a cryoprotectant solution and later thawed. The thawed embryos have a reasonably good viability rate and are transferred to the uterus of recipient animals for further gestation. The typical procedure in the embryo transfer industry requires a serial rehydration of embryos following thawing. The embryo must be removed from the freezing container, and handled by a technician. The process can take at least 30 to 40 minutes. The complicated transfer methods devised by prior investigators in this field require the concentration of cryoprotectant in the embryo freezing solution to be decreased slowly after thawing to avoid lysing embryonic cell membranes. See e.g. Miyamoto, H. and Ishibashi, T., "The Protective Action of Glycols Against Freezing Damage of Mouse and Rat Embryos", *J. Reprod. Fert*, 54: 427-32 (1978). This "step-wise rehydration" of the embryo has been assumed to be a necessary part of embryo handling. More recently, some investigators have rehydrated thawed embryo cells using sucrose as an osmotic buffer. Renard, J., Ozil, J., and Heyman, Y., "Cervical Transfer of Deep Frozen Cattle Embryos", *Theriogenology*, 15: 311-320 (1981).

In an embryo transfer technique, the primary means for cryopreservation of mammalian embryos employs the use of permeating cryoprotective agents. Glycerol is the most commonly used cryoprotectant today. Under the "step-wise rehydration" technique, embryos are most often frozen in semen straws, and upon thawing, are removed from the straws through a series of solutions containing decreasing concentrations of cryoprotectant and then reloaded into a semen straw for nonsurgical transfer to a recipient female. All embryo handling procedures require the use of a microscope, sterile supplies and solutions, and must be performed by a skilled technician trained in these procedures. Therefore, developing a process by which the frozen embryo can be thawed within the straw and transferred directly to a recipient female without seriously diminishing pregnancy rates would be very important commercially.

Currently, the most commonly employed cryoprotective agent is glycerol. Leibo, S. P. "A One-Step Method for Direct Nonsurgical Transfer of Frozen-Thawed Bovine Embryos", *Theriogenology*, 21: 767-90 (1984). Among the other cryoprotectants investigators have looked at using is ethylene glycol, which has been researched as a cryoprotectant for mammalian embryos, but not using a direct transfer method. Heyman, Y., Vincent, C., Garnier, V., and Cognie, Y., "Transfer of Frozen-Thawed Embryos in Sheep", *Veterinary Record*, 120: 83-85 (1987). The procedure published by Y. Heyman, et al, in 1987, using ethylene glycol as a cryoprotectant for sheep embryos, requires a "one-step" dilution or rehydration with sucrose. Other investigators found ethylene glycol to be a good cryoprotectant for murine embryos, but their method still requires a three-step rehydration with a modified Krebs-Ringer bicarbonate medium. Miyamoto, H. and Ishibashi, T. "The Protective Action of Glycols Against Freezing Damage of Mouse and Rat Embryos", *J. Reprod. Fert.*, 54: 427-32 (1978). Miyamoto, H. and Ishibashi, T., "Survival of Frozen-Thawed Mouse and Rat Embryos in the Presence of Ethylene Glycol", *J. Reprod. Fert.*, 50: 373-75 (1977). Other investigators have looked at direct transfer methods, but these experiments have required a combination of glycerol and sucrose as the cryoprotective agent. Massip, A., Van Der Zwalmen, P. and Ectors, F., "Recent Progress in Cryopreservation of Cattle Embryos", *Theriogenology*, 27: 69-79 (1987).

One rehydration technique referred to as the "one-step" method has one rehydration step rather than a multiple step-wise rehydration. Leibo, S. P. "Embryo Transfer Method and Apparatus", U.S. Pat. No. 4,380,997, issued Apr. 26, 1983. However, even the "one-step" method involves special handling of embryos in the field because it still requires dilution of the cryoprotectant upon thawing. Although patented and described in the scientific literature, the results of this procedure "have been less than satisfactory in that only a 26% pregnancy [rate] has been achieved overall." Leibo, S. P. "A One-Step Method for Direct Nonsurgical Transfer of Frozen-Thawed Bovine Embryos", *Theriogenology*, 21: 767-90 (1984). Leibo reported highly variable results for individual sets of frozen-thawed embryos with pregnancy rates ranging from 0% and 6% to 55% and 63%. It is believed that the technician performing the thaw exerts a significant effect on pregnancy rates suggesting that this procedure is too elaborate to be reproducible enough to meet commercial needs.

SUMMARY OF THE INVENTION

The improved direct transfer method for embryonic cryopreservation and subsequent transfer to a recipient animal allows the embryos to be thawed within the cryoprotective container and successfully transferred directly from the container to the recipient animal without a rehydration process. The direct transfer method has been tested on bovine embryos and also will have future application to the embryos of other mammalian species. The present invention includes an improved method for thawing frozen embryos and transferring them at the field location of the recipient animal with consistent and successful results. The direct transfer method is a great advantage since present techniques require either a multi-step or one-step dilution process to remove the cryoprotective agent from the embryo such that the ability of the technician performing the dilution and transfer may significantly impact pregnancy rates.

In the present invention, embryos are collected, placed in a cryoprotective solution of from about 1.0 M to about 2.0 M ethylene glycol, or glycerol or any combination thereof in an isotonic salt solution in containers suitable for cryopreservation that preferably allow for direct transfer to recipient animals. A preferred cryoprotective solution is about 1.5 M ethylene glycol in an isotonic salt solution. The embryos are then equilibrated and frozen for a desired length of time in liquid nitrogen. Upon thawing, the embryo in the cryoprotective container can be transferred directly to a recipient animal or to an in vitro culture system.

The present invention can also include use of embryos produced by various in vitro techniques including nuclear transfer, embryo splitting, fertilization of in vitro matured oocytes, in vitro fertilization of oocytes, in vitro culture of fertilized oocytes, gene transfer of exogenous DNA to an embryo, and artificial insemination. These techniques are of increasing commercial importance.

In addition, other methods of the invention include the additional step of exposing the embryos to various pretreatments of proteolytic enzymes such as pronase, trypsin, and chymotrypsin; detergents; and organic solvents such as ethanol and methanol. These pretreatments increase membrane permeability by either removing proteins from the cell membranes or solubilizing lipids in the cell membranes. Enhancing membrane permeability reduces osmotic shock to the embryo during equilibration of the embryo in the cryoprotective solution and during rehydration of the embryo in the recipient animal's uterus following direct transfer to the recipient.

An alternative method of the invention includes the additional step of combining the embryos with pieces of trophoblastic tissue from another viable embryo prior to equilibration. Trophoblastic tissues give rise to the placental membrane in a developing fetus. These tissues are a source of the signals which maintain pregnancy in most animals. The extra trophoblastic tissues provide signals that supplement the signals of the trophoblastic tissues of the embryo of merit, and will enhance pregnancy rates.

The direct transfer method allows the rehydration step after thawing to be eliminated, thus allowing direct transfer of the embryo to the recipient animal. It is no longer necessary to use a diluent such as sucrose in an isotonic salt solution in the cryoprotective container to dilute away the cryoprotective agent in the present invention. Prior methods require the dilution of the cryoprotective agent, usually glycerol, from the embryo prior to transfer to the recipient animal using either a step-wise or one-step rehydration technique. The one-step technique which allowed for the dilution of the cryoprotectant from the embryo within the cryoprotective container required mixing of the container contents prior to transfer of the embryo to the recipient. The present invention eliminates both the dilution step and the mixing step that were required by the "one-step" method. Furthermore, the present invention eliminates the need for a combination of glycerol and sucrose in the cryoprotective solution in order to accomplish a direct transfer such as described by Massip, et al.

DESCRIPTION OF THE PREFERRED METHOD

Figure 1:
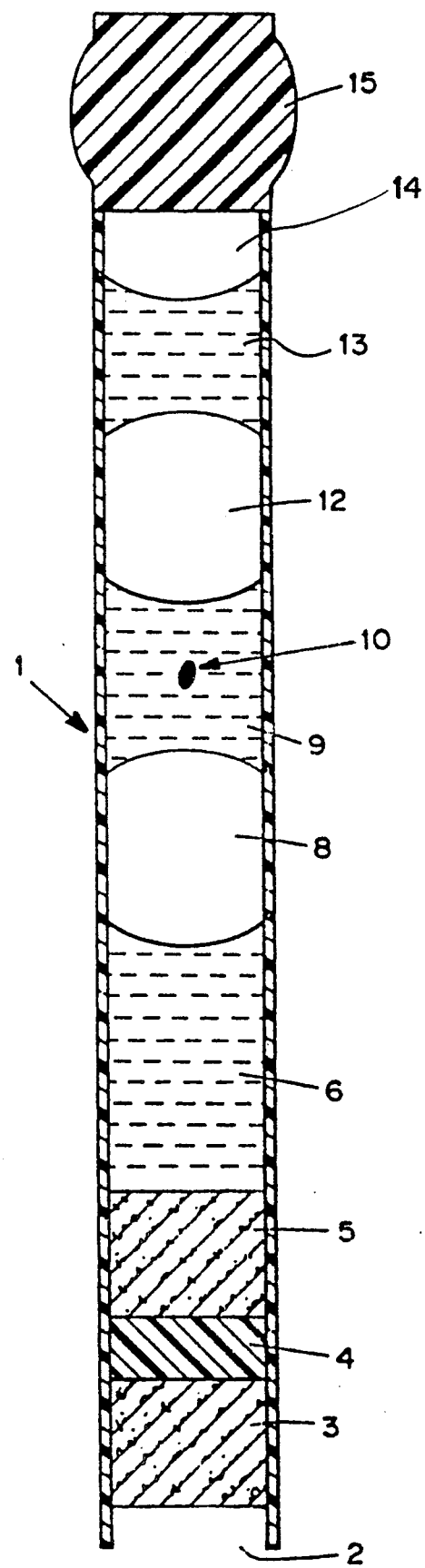
FIG. 1 is a cross-sectional schematic view of an elongated tubular cryoprotective container (straw), having three (3) chambers, with the embryo in cryoprotective solution in the middle chamber.

The method involves several steps which generally include collecting embryos, placing the embryos in a cryoprotective solution of ethylene glycol, glycerol, or any combination thereof in an isotonic salt solution in a cryoprotective container, allowing the embryos to equilibrate in the cryoprotectant, freezing the embryos for a desired time period in liquid nitrogen, thawing the embryos, and directly transferring the thawed embryos to the recipient animals.

The embryos are collected from artificially inseminated animals as well as created by in vitro procedures, including in vitro fertilization of in vivo and in vitro matured oocytes, in vitro culture of fertilized oocytes, embryo splitting, and nuclear transfer. Any method to produce properly aged embryos may be used.

The embryo splitting technique is well-known to those skilled in the art. One preferred method of embryo splitting involves cutting normal 6 to 8 Day embryos into two pieces with a micromanipulator. Monozygotic twins are thereby induced. The other methods of producing embryos are discussed in more detail subsequently.

The embryos used for the direct transfer technique can also be produced by gene transfer to in vitro cultured embryos. Such embryos are microinjected with foreign DNA to produce a transgenic embryo which can be subsequently cultured in an appropriate culture medium or in vivo.

In vitro cultured embryos have improved viability after freezing when cultured prior to freezing in a preferred co-culture system. The preferred culture for in vitro grown embryos prior to freezing is a Buffalo rat liver (BRL) co-culture system. One preferred BRL co-culture system is made by filling culture dishes with $2 \times 10^5$ BRL 3A cells (American Type Culture Collection in Rockville, Md.) and 0.5 ml of fresh media such as M199 (GIBCO in Grand Island, N.Y.) with 1% bovine serum albumin (BSA) and 10% fetal calf serum (FCS), conditioned for 24 hours and maintained with 5% $CO_2$ in air. During the 24 hour conditioning period, the BRL cells attach (or plate) to the surface of the culture dish and form what is generally referred to as a feeder layer. Other concentrations of BRL cells may be plated depending upon when the culture wells are made and when they are used. Fewer cells are plated when the time prior to use of the wells in co-culture is lengthened.

Another preferred method of making the BRL co-culture system involves using Whitten's medium, rather than M199, to culture the BRL cells in 1% BSA and 10% FCS. Whitten's medium is well-known to those skilled in the art.

The embryos to be frozen are placed in a cryoprotective container with a cryoprotectant mixed with a cell culture media of an isotonic salt solution. The isotonic salt solution generally has an osmolality of 250 to 350 milliosmoles, a pH in the range of 6.8 to 7.6, a pH buffer, and is supplemented with a protein source or a synthetic macromolecule such as polyvinylpyrrolidone. The solution may contain individual nutrients such as carbohydrates, amino acids and vitamins. The most common salt solution used for freezing embryos is Dulbecco's phosphate buffered saline with common modifications of 0.4% bovine serum albumin, 0.1% glucose, and 0.036% sodium pyruvate (the solution hereinafter referred to as PB1).

A cryoprotective solution using one cryoprotectant is in the range of about 1 M to about 2 M. When the cryoprotective solution is a combination of cryoprotectants from the group of ethylene glycol, and glycerol, the primary cryoprotectant in the solution will be ethylene glycol supplemented with a lower concentration of the glycerol. In one preferred method, ethylene glycol will be in the range of about 1.0 M to 1.25 M, and the glycerol, that is combined with the ethylene glycol, will be in the range of about 0.5 M to 0.25 M. The combination of cryoprotectants will be in the isotonic salt solution that was already discussed.

Other methods of the invention include the additional step of exposing the embryos to various pretreatments of proteolytic enzymes such as pronase, trypsin, and chymotrypsin; detergents; and organic solvents such as ethanol and methanol. These pretreatments increase membrane permeability by either removing proteins from the cell membranes or solubilizing lipids in the cell membranes. Enhancing membrane permeability reduces osmotic shock to the embryo during equilibration of the embryo in the cryoprotective solution and during rehydration of the embryo in the recipient animal's uterus following direct transfer to the recipient.

An alternative method of the invention includes the additional step of combining the embryos with pieces of trophoblastic tissue from different viable embryos prior to equilibration of the embryo in the cryoprotective solution. As discussed before, trophoblastic tissues give rise to the placental membranes in a developing fetus and are a source of the signals which maintain pregnancy in most animals. This is generally known to those well-skilled in the art.

In one preferred method, the trophoblastic tissue can be freshly dissected from a viable embryo at about Day 13 to Day 14 or it can be dissected and cultured for twenty-four hours in a suitable culture medium such as tissue culture medium (TCM) 199 supplemented with 10% fetal calf serum (FCS). The trophoblastic tissue is combined with the embryo in the cryoprotective solution and otherwise processed according to the methods of this invention. The trophoblastic tissue and embryo therefore can be directly transferred from the cryoprotective container to the uterus of the recipient animal.

After the embryos are placed in the cryoprotective solution they are allowed to equilibrate for about 5 to 40 minutes in the temperature range of above 0° C. to 39° C. Preferably the equilibration time is in the range of about 10 to about 20 minutes, and the equilibration temperature is in the range of about 18° C. to 25° C. In general, the appropriate equilibration time will depend on the environmental conditions which the embryos are subjected to; i.e., the concentration of cryoprotectant and the temperature at which equilibration is performed. Generally, as the cryoprotectant concentration increases, the time required for equilibration decreases, and vice versa. Furthermore, as the temperature increases, the equilibration time required decreases. The term "equilibrate" as used herein means the interior of the embryo is accumulating cryoprotectant in order to reach a condition of relative balance with the cryoprotective solution.

The placement of the embryo in the cryoprotective solution takes place in a petri dish with subsequent equilibration preferably taking place in a container suitable for cryopreservation that allows for direct transfer to recipient animals. The preferred embodiment is a cryoprotective container in a tubular shape and made of a biocompatible plastic that can be inserted into a standard artificial insemination gun or an artificial insemination gun modified for embryo transfer (hereinafter referred to as an artificial insemination gun). This allows the embryo to remain in the container throughout freezing, thawing, and transfer procedures thereby eliminating handling of the embryo.

One preferred process of the invention employs the use of sterile plastic semen straws commercially available and commonly used in the artificial insemination industry. Such straws are familiar to those skilled in the art. The straws are available in a variety of sizes, and the 0.25 ml and 0.50 ml capacity straws are suitable for the present invention.

Referring to FIG. 1, one preferred embodiment of the cryoprotective container is shown after the embryo has been prepared for freezing. FIG. 1 is a cross-section of a tubular container 1, which represents a suitable structure, such as the plastic semen straws previously mentioned. FIG. 1 depicts the tubular container 1 after the embryo 10 has been placed inside and sealed. The tubular container 1 is closed at one end 2 by a layer of porous sealing plug material 3, which could be cotton, a sealant 4 above that, and another layer of porous sealing plug material 5 above that. The preferred sealant 4 is a dry powder material such as polyvinyl chloride which solidifies and seals once it becomes moist. The tubular container 1 has an open end opposite to end 2 for receiving the appropriate volumes of liquid and embryo. The first column of liquid 6 above the plug material 5 contains isotonic salt solution or the cryoprotective solution. Above the first column of liquid is a second column of liquid 9 which is separated from the first by an air bubble 8. The second column of liquid 9 is a cryoprotective solution which contains the embryo 10. An air bubble 12 separates the second column of liquid 9 from a third column of liquid 13. The third column of liquid may be isotonic salt solution or cryoprotective solution. Typically, the third or top column 13 contains the isotonic salt solution. The overall ratio of the isotonic salt solution to the cryoprotective solution in the container is in the range of about 1:1 to 5:1. An air space 14 separates the third column of liquid 13 from the upper end of the tubular container. The upper end of the tubular container is heat sealed by melting the end of the plastic straw to form a seal 15. The solutions in the third column 13 and first column 6 of the container help to assure that the embryo is expelled from the gun when transferred to the recipient.

One preferred technique for loading the container shown in FIG. 1 is to use a syringe attached to end 2 to first draw the isotonic salt solution into the container to form the first column 6, then to allow the container to aspirate air bubble 8. A syringe is used to introduce the volume 9 of cryoprotective agent containing the embryo 10 into the container. Next, the container should be allowed to aspirate another air bubble 12, and finally the isotonic salt solution or the cryoprotective solution 13 should be drawn into the container with the syringe. An air space 14 is left above volume 13, and continued aspiration with the syringe will cause the isotonic salt solution in column 6 to contact layers 5 and 4 so that the sealant 4 solidifies. The container can then be heat sealed.

Figure 2:
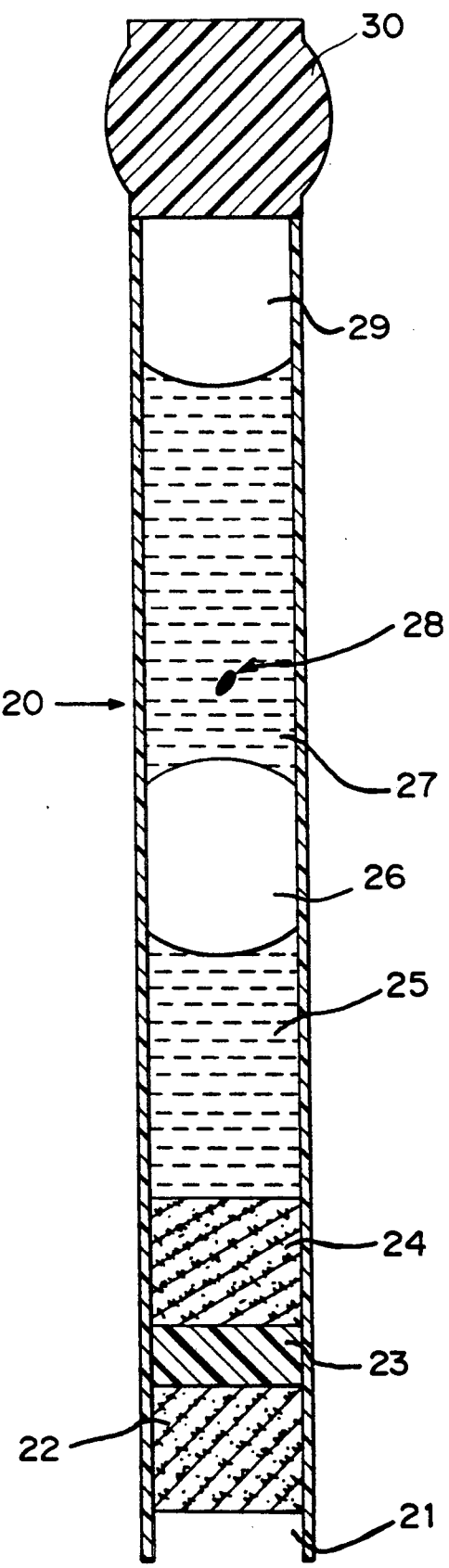
FIG. 2 is a cross-sectional schematic view of a two-chambered straw with the embryo in the cryoprotective solution.

Referring to FIG. 2, another preferred embodiment of the cryoprotective container is shown which has two chambers after the embryo has been prepared for freezing. FIG. 2 is a cross-section of a tubular container 20, which represents a suitable structure, such as the plastic semen straws previously described. FIG. 2 depicts the tubular container 20 after the embryo 28 has been placed inside and sealed. The tubular container 20 is closed at one end 21 by a layer of porous sealing plug material 22, which could be cotton, sealant 23 above that, and another layer of porous sealing plug material 24 above that. The preferred sealant 23 is a dry powder material such as polyvinyl chloride which solidifies and seals once it becomes moist. The tubular container 20 has an open end opposite to end 21 for receiving the appropriate volumes of liquid and embryo. The first column of liquid 25 above the plug material 24 contains isotonic salt solution. Above the first column of liquid 25 is a second column of liquid 27 which is separated from the first column 25 by an air bubble 26. The second column of liquid 27 is a cryoprotective solution which contains the embryo 28. An air space 29 separates the second column of liquid 27 from the upper end of the tubular container 30. The overall ratio of the isotonic salt solution to the cryoprotective solution in the container is in the range of about 1:1 to 5:1. The upper end of the tubular container is heat sealed by melting the end of the plastic straw to form a seal 30.

One preferred technique for loading the container shown in FIG. 2 is similar to the preferred technique for loading the container shown in FIG. I. A syringe is used to first draw the isotonic salt solution into the container to form the first column 25, then to allow the container to aspirate air bubble 26. A syringe is then used to introduce the volume 27 of cryoprotective agent containing the embryo 28 into the container. The air space 29 is left above volume 27, and continued aspiration with the syringe will cause the isotonic salt solution in column 25 to contact layers 24 and 23 so that the sealant 23 solidifies. The container can then be heat sealed.

When the cryoprotective container shown in FIG. 1 or FIG. 2 is ready to be loaded into the artificial insemination gun, the heat sealed end 15 or 30 can be cut off and then the tubular container can be placed into the artificial insemination gun. The artificial insemination gun pushes the sealing plug (encompassed by 3, 4 and 5 or 22, 23 and 24) through the interior diameter of the tubular container forcing all of the liquid material in the container out its open end directly into the recipient animal.

Freezing the embryos involves first cooling them in a controlled rate freezer. The embryos can be either placed directly into the freezing apparatus at a temperature slightly below the freezing point of the cryoprotective solution, which is called the seeding temperature, or can be cooled at a controlled rate of about $-1°$ C./minute to the seeding temperature. The seeding temperature is normally in the range of about $-5°$ C. to $-8°$ C. and is dependent upon the type and concentration of the cryoprotectant solution used. The embryos are held at this seeding temperature long enough to reach thermal equilibrium between the container and the freezer chamber which usually takes from about 1 to about 2 minutes. Ice nucleation is then induced by touching the container with a metal instrument previously supercooled in liquid nitrogen. The embryos are then cooled further at a controlled rate in the range of about $-0.1°$ C./minute to about $-1.0°$ C./minute until the embryos are in the range of about $-20°$ C. to $-40°$ C. One preferred method of the invention is to further cool the embryos after ice nucleation at the controlled rate of $-0.3°$ C./minute to $-0.7°$ C./minute to an end point temperature in the range of about $-25°$ C. to about $-35°$ C. Once the embryos reach the end point temperature, they can be plunged immediately into liquid nitrogen or held at the endpoint temperature for a varying period of time prior to plunging, the preferred length of the hold being 15 minutes.

When the time comes to remove the embryos from storage in liquid nitrogen for transfer to recipient animals, the thawing procedure chosen should be suitable for the freezing procedures employed; i.e., the insulating properties of the container, the cooling rates used and the terminal temperature at which the embryo is plunged into liquid nitrogen. It is generally accepted that when an embryo is slow cooled to an endpoint temperature below $-40°$ C. (usually to $-60°$ C. to $-80°$) before plunging the embryo into liquid nitrogen, a slow thaw rate (relative to the thaw rate required if the embryo is plunged into liquid nitrogen at a temperature greater than $-40°$ C.) is required to maintain embryo viability.

The thawing procedures for embryos plunged in liquid nitrogen at temperatures greater than $-40°$ C. may range from placing the cryoprotective container in air at room temperature to placing the container in a water bath of up to 40° C. In the preferred method of this invention the cryoprotective containers are placed into a water bath of about 30° C. for about 10 seconds.

As discussed before, the thawed embryo is then directly transferred to the recipient animal. In the preferred method, this transfer is done immediately upon removal of the container from the water bath. Generally, this is done by loading the cryoprotective container into an artificial insemination gun and using the gun to deposit the embryo into the uterus of a suitable recipient female. Furthermore, the direct transfer step may include transferring the embryo from the cryoprotective container directly to an in vitro culture system such as PB1 for brief viewing or such as the BRL co-culture for longer observation. After transfer to a culture system such as the BRL co-culture, the embryo is then, at a desired stage in its development, transferred to a recipient animal. The ultimate recipient is an animal of the same species as the embryo.

The following examples are provided to facilitate the understanding of preferred methods of the present invention and not for the purpose of limiting same. Those skilled in the art will recognize that various modifications in the procedure previously discussed and outlined below can be used for the purpose of practicing the present invention.

EXAMPLE 1

Bovine embryos can be collected in the range of Day 6 to Day 8 of the donor estrous cycle in the morula to hatched blastocyst stage, but in the preferred method are collected at Day 7 to Day 7½ in the late morula to expanded blastocyst stage, placed in a cryoprotective solution of 1.5 M ethylene glycol in PB1, and loaded into a 0.25 ml plastic semen straw with a section of a 0.5 ml semen straw fitted over the sealed end for use as a handle and a labelling surface (Continental Plastics or I.M.V.). Next the embryos are allowed to equilibrate for ten minutes at room temperature. The freezing procedure for the embryos involves cooling the embryos in a controlled rate freezer to −7° C. and holding at that temperature for two minutes, inducing ice nucleation by touching the outside of the straw at the level of any column of liquid, but usually the top column, with a supercooled metal instrument such as metal forceps, holding the embryos for five minutes at −7° C., cooling the embryos at a controlled rate of −0.5° C./minute to an end point temperature of −35° C., holding the embryos at −35° C. for 15 minutes, and then plunging the embryos into liquid nitrogen for final storage.

At the appropriate time for transfer of the embryos to the recipient animal, the embryos are thawed by placing the semen straws into a water bath of about 30° C. for ten seconds. The top end of the straw is then snipped off just below the heat seal and the straw is inserted into an artificial insemination gun. The entire contents of the straw are transferred to the uterus of an appropriate recipient animal by causing the plunger of the artificial insemination gun to push the plug at the bottom end of the straw through the length of the straw delivering the liquid contents and embryo out the open cut off end of the straw into the uterus of the animal.

Tables 1 and 2 show the results of this preferred method of the invention. Table 1 shows viability rates of the previously frozen embryos after direct rehydration in PB1 and transfer to an in vitro culture. For the purposes of in vitro assessment of embryo viability, the act of rehydrating embryos directly in PB1 is considered analogous to direct transfer of the embryo to the uterus of a recipient female. Table 2 shows pregnancy rates resulting from direct transfer to a recipient cow. In these tables and the subsequent tables, the results of the preferred method are compared to a control of 10% glycerol using a three-step rehydration procedure unless otherwise specified. This control was chosen because it is representative of the common practices in the commercial embryo transfer industry.

Table 1 below shows bovine embryo viability at 24, 48 and 72 hours for embryos in a culture medium with the number of viable embryos compared to the number of embryos frozen and the percentage of viable embryos listed in parentheses. Embryos frozen in glycerol were rehydrated using a step-wise procedure. Embryos frozen in 1.5 M ethylene glycol were rehydrated directly with PB1 and then transferred into tissue culture media (TCM) 199 with 10% FCS and a feeder layer of BUC. The feeder layer can be BRL cells.

TABLE 1

IN VITRO DEVELOPMENT OF EMBRYOS FROZEN IN ETHYLENE GLYCOL AND REHYDRATED DIRECTLY

| Cryoprotectant | No. Viable/No. Frozen (%) | | |
|---|---|---|---|
| | 24 hours | 48 hours | 72 hours |
| Direct Rehydration 1.5 M Eth. Gly. | 24/25 (96) | 23/25 (96) | 22/25 (88) |
| Step-wise Rehydration 10% Glycerol | 6/7 (86) | 6/7 (86) | 6/7 (86) |

These results demonstrate that embryos have a high survival rate with direct rehydration when frozen in 1.5 M ethylene glycol.

Table 2 below shows bovine pregnancy rates, which are the number of bovine pregnancies compared to the number of embryos transferred to recipients, for straws loaded with different solutions. The first two columns of data represent two means of practicing the present invention. The first column of data in Table 2 is for a straw loaded with 1.5 M ethylene glycol in columns 6, 9 and 13 of FIG. 1. The second column of data in Table 2 shows pregnancy rates for a straw loaded with 1.5 M ethylene glycol in columns 9 and 13 of FIG. 1 and PB1 in column 6 with the ratio of the total volume of ethylene glycol to PB1 being 1:3 in Replicate I and 1:5 in Replicate II. The embryos described in the first two column of Table 2 were transferred directly following thawing. The third column of data is for a straw loaded with 10% glycerol in all three columns. Embryos frozen in glycerol were rehydrated using a three-step procedure.

TABLE 2

PREGNANCY RATES AT ABOUT 55 TO 60 DAYS FOR DIRECT TRANSFER

| | No. pregnant/No. transferred | | |
|---|---|---|---|
| Replicate | Direct 1.5 M Eth. Gly. | Direct 1.5 M Eth. Gly./PB1 | Step-wise 10% Glycerol |
| I | 10/26 | 12/24 | 20/35 |
| II | — | 7/26 | 5/24 |
| Total (%) | 10/26 (38%) | 19/50 (38%) | 25/59 (42%) |

The results in Table 1 indicate higher viability for embryos in 1.5 M ethylene glycol rather than 10% glycerol after direct transfer to an in vitro culture. The data on pregnancy rates in Table 2 shows similar results for 1.5 M ethylene glycol and 10% glycerol.

Of the pregnancies resulting from the direct transfers in Replicate I shown in Table 2, two were selected at random to proceed as normal pregnancies, and 2 normal calves were born. The remaining pregnancies were proceeding normally at greater than 55 days of gestation.

EXAMPLE 2

The following is an alternative method using a cryopreservation pretreatment of trypsin.

This method is accomplished by following the steps of Example 1 with the additional step of exposing the embryos to a solution containing trypsin in the range of about 0.05% to 0.5% in an isotonic salt solution prior to equilibrating the embryos in the cryoprotective solution. The embryos are washed in trypsin using a procedure similar to the one recommend by the International Embryo Transfer Society (IETS). This procedure involves washing the embryos five times in Dulbecco's phosphate buffered saline with 0.4% bovine serum albumin (BSA), washing the embryos two times (60 to 90 seconds each) in 0.25% trypsin in calcium and magnesium-free Hank's balanced salt solution (HBSS), and then washing the embryos five times in calcium and magnesium free Dulbecco's phosphate buffered saline with 10% fetal calf serum (FCS). Control embryos are subjected to the same procedure, except that trypsin is deleted from the HBSS.

Table 3 shows the effect of trypsin washing on the in vitro development of embryos frozen in ethylene glycol and rehydrated directly in a culture medium. At 24, 48 and 72 hours of culture, the number of viable bovine embryos pretreated with trypsin prior to processing for freezing and direct rehydration is compared to the viability of embryos not pretreated with trypsin. The percentage of viable embryos is shown in parentheses.

TABLE 3

EFFECT OF TRYPSIN WASHING ON IN VITRO DEVELOPMENT OF EMBRYOS FROZEN IN ETHYLENE GLYCOL AN REHYDRATED DIRECTLY

| Treatment | No. viable/No. thawed (%) | | |
|---|---|---|---|
| | 24 hours | 48 hours | 72 hours |
| Trypsin washed 1.5 M ethylene glycol | 30/40 (75) | 30/40 (75) | 28/40 (70) |
| Control washed 1.5 M ethylene glycol | 32/40 (80) | 32/40 (80) | 26/40 (65) |

The data shows that trypsin pretreatment of embryos may be performed with the direct transfer technique of the present invention.

EXAMPLE 3

The following example is one preferred embodiment of the present invention in which the steps of Example 1 are followed and the direct transfer step includes the additional step of transferring the embryo from the cryoprotective container to an in vitro culture system of PB1 for a desired time period prior to transferring to the recipient animal. After transfer from the straw to PB1 the embryo can be briefly observed to assess viability and then loaded into another container for transfer to a recipient or held in culture for an extended period of time prior to transfer. In the case of the latter, the culture system would preferably consist of a bicarbonate buffered medium generally accepted for use in long-term culture of embryos and with or without feeder cells such as BUC or BRL cells.

EXAMPLE 4

The following example illustrates varying concentrations of the preferred cryoprotectant, ethylene glycol. The steps of Example 1 were followed. The cryoprotectant is ethylene glycol in the range of about 1.0 M to about 2.0 M in PB1.

Tables 4 and 5 below show bovine embryo viability at 24, 48 and 72 hours of culture after freezing in different concentrations of ethylene glycol in the cryoprotective solution, thawing and direct rehydration. Table 4 compares direct rehydration data with 10% glycerol three-step rehydration data.

TABLE 4

IN VITRO DEVELOPMENT OF EMBRYOS FROZEN IN 1.0 M, 1.5 M, AND 2.0 M ETHYLENE GLYCOL AND REHYDRATED DIRECTLY

| Cryoprotectant | No. viable/No. frozen (%) | | |
|---|---|---|---|
| | 24 hours | 48 hours | 72 hours |
| Direct Rehydration | | | |
| 1.0 M Eth. Gly. | 14/20 (70) | 12/20 (60) | 11/20 (55) |
| 1.5 M Eth. Gly. | 17/20 (85) | 17/20 (85) | 16/20 (80) |
| 2.0 M Eth. Gly. | 8/25 (32) | 12/25 (48) | 8/25 (32) |
| Step-wise Rehydration | | | |
| 10% Glycerol | 5/8 (63) | 5/8 (63) | 5/8 (63) |

TABLE 5

IN VITRO DEVELOPMENT OF EMBRYOS FROZEN IN 1.25 M, 1.5 M, AND 1.75 M ETHYLENE GLYCOL AND REHYDRATED DIRECTLY

| Cryoprotectant | Rep. | No. viable/No. frozen (%) | | |
|---|---|---|---|---|
| | | 24 hours | 48 hours | 72 hours |
| 1.25 M Eth. Gly. | | 14/26 (54) | 14/26 (54) | 9/26 (35) |
| 1.5 M Eth. Gly. | | 18/26 (69) | 16/26 (62) | 13/26 (50) |
| 1.75 M Eth. Gly. | | 16/26 (62) | 15/26 (58) | 9/26 (35) |

The preferred concentration is about 1.5 M ethylene glycol based upon the ranges of ethylene glycol tested.

EXAMPLE 5

Another alternative method of the present invention is shown in the following example. The steps of Example 1 are followed using different cryoprotective solutions of 10% glycerol, 1.5 M propylene glycol in PB1 and 1.5 M DMSO in PB1.

Table 6 below shows bovine embryo viability at 24, 48 and 72 hours of culture post-thaw for embryos frozen in these cryoprotective solutions.

TABLE 6

IN VITRO DEVELOPMENT OF EMBRYOS FROZEN IN GLYCEROL, ETHYLENE GLYCOL, PROPYLENE GLYCOL OR DMSO AND REHYDRATED DIRECTLY

| Cryoprotectant | No. viable/No. frozen (%) | | |
|---|---|---|---|
| | 24 hours | 48 hours | 72 hours |
| 10% Glycerol | 6/10 (60) | 3/10 (30) | 3/10 (30) |
| 1.5 M Eth. Gly. | 16/20 (80) | 15/20 (75) | 14/20 (70) |
| 1.5 M DMSO | 7/20 (35) | 7/20 (35) | 5/20 (35) |
| 1.5 M Prop. Gly. | 3/19 (16) | 3/19 (16) | 2/19 (11) |

All embryos were rehydrated directly in PB1 holding medium after thawing, including the embryos in glycerol. This experimental data shows that the direct rehydration procedure does work with other cryoprotectants but not as well as with ethylene glycol.

EXAMPLE 6

The embryos used for the direct transfer technique can be developed using nuclear transfer techniques. The donor cell, typically an embryonic cell, is fused to an enucleated egg thereby transferring the nuclear material. A nuclear transfer procedure for bovine embryos is described in Bovine Nuclear Transplantation, Massey and Willadsen, PCT published application WO 88/09816, 15 Dec. 1988 which is incorporated by reference herein. Those skilled in the art are familiar with other nuclear transfer procedures.

Table 7 shows in vitro development of cloned embryos produced by nuclear transfer frozen in 10% glycerol and rehydrated using the step-wise procedure compared to cloned embryos produced by nuclear transfer, frozen in 1.5 M ethylene glycol, thawed, and rehydrated directly in the culture medium. Embryo viability is shown at 24, 48 and 72 hours of culture after thawing.

TABLE 7

IN VITRO DEVELOPMENT OF EMBRYOS PRODUCED BY NUCLEAR TRANSFER, FROZEN IN ETHYLENE GLYCOL, AND REHYDRATED DIRECTLY

| Cryoprotectant | No. viable (%) | | |
|---|---|---|---|
| | 24 hours | 48 hours | 72 hours |
| Direct Rehydration | | | |
| 1.5 M Eth. Gly. | 18/28 (64) | 14/28 (50) | 14/28 (50) |
| Step-wise Rehydration | | | |
| 10% Glycerol | 14/27 (52) | 13/27 (48) | 13/27 (48) |

Embryos frozen in glycerol were rehydrated using a step-wise procedure. Embryos frozen in 1.5 M ethylene glycol were rehydrated directly in PB1 medium and transferred into a cell culture medium of tissue culture medium (TCM) 199 with 10% FCS and a feeder layer of BUC. The data shows that the direct transfer procedure is successful on nuclear transfer embryos.

Table 8 shows the pregnancies achieved in a first trial of direct transfer of cloned embryos produced by nuclear transfer to recipient females.

TABLE 8

PREGNANCY RATES AT 55 TO 60 DAYS AFTER DIRECT TRANSFER OF NUCLEAR TRANSFER EMBRYOS

| Replicate | Step-wise Rehydration 10% Glycerol | Direct Eth. Gly. |
|---|---|---|
| I | 2/31 | 9/38 |
| II | 16/45 | 10/46 |
| Total | 18/76 (24) | 19/84 (23) |

Embryos frozen in glycerol were rehydrated using a step-wise procedure. All others were transferred directly following thawing. This data illustrates that the direct transfer procedure has value for cryopreservation of nuclear transfer embryos. Three recipient females pregnant with calves produced from direct transfer of nuclear transfer embryos gave birth to two normal calves and one premature calf. Other pregnancies are progressing at this time.

In another embodiment of the invention, early stage embryos are non-surgically recovered from donor females at Day 5.0 to 5.5 (instead of Day 6.0 to 8.0) following estrus. The embryos are frozen in 1.5 M ethylene glycol for direct rehydration. The thawed embryos are then used as blastomere cell donors in nuclear transfer procedures. Experimental results show that 1.5 M ethylene glycol and direct rehydration works as well or better than 10% glycerol and step-wise rehydration for cryopreservation of early stage embryos for use as a source of viable cells for nuclear transfer.

EXAMPLE 7

The embryos used for the direct transfer technique can be developed using embryos that are cultured in vitro for part or all of the time to the desired age for cryopreservation. The fertilized eggs are placed in the appropriate culture medium for development. Many techniques and culture media are known in the art. A method for bovine development is described in Bovine Embryo In Vitro Culture, Bondioli, PCT published Application WO 89/07135, 10 Aug. 1989 which is incorporated by reference herein. References to other embryo culture systems are included in WO 89/07135 and are exemplary of alternative methods.

The preferred embodiment for in vitro cultured embryos includes the steps of Example 1 with the additional step of co-culturing embryos produced from in vitro matured oocytes which have been in vitro fertilized with a BRL culture system.

The BRL co-culture wells are prepared by plating $2 \times 10^5$ BRL 3A cells (American Type Culture Collection in Rockville, Md.) in wells of 4-well culture dishes with 0.5 ml of fresh M199 medium with 10% FCS and 1% BSA for 24 hours prior to use. During this conditioning period and for the duration of cultures, the plates are maintained within modular incubator chambers purged with 5% $CO_2$ in air. BRL cells attach to the surface of the culture dish during this conditioning period.

The fertilized ova are vortexed 18 hours post-insemination to remove cumulus cells and washed in an excess of TL-Hepes. The fertilized ova are then placed into the culture wells at a maximum of 25 ova per well. The culture plates are then returned to the 5% $CO_2$ in air atmosphere. After 72 hours of culture, all embryos are moved to fresh wells prepared 24 hours in advance and maintained for the final 4 days of culture. Thereafter, the embryos are placed in the cryoprotective solution, equilibrated, and otherwise submitted to the direct transfer method, in accordance with the steps of Example 1. The embryos may be rehydrated directly in PB1 medium, as an alternative, so that embryo post-thaw viability may be checked.

In vitro cultured embryos have been rehydrated directly prior to transfer to recipient animals and inspected for viability and other valuable information. Embryos produced by in vitro culture in the BRL co-culture system survive freezing and rehydration at a rate of 50% or more compared to survival rates of about 10% for embryos produced by in vitro co-culture with other co-culture media. To further define optimum conditions for rehydration of embryos produced by in-vitro co-culture with BRL cells, a comparison was made of three rehydration techniques. Direct rehydration with PB1 was compared experimentally with step-wise rehydration in 0.75 M ethylene glycol for 5 minutes followed by transfer to PB1, and with one-step rehydration with iso-osmolar sucrose for 5 minutes. Following rehydration, all embryos were put into a BRL co-culture to assess viability. Experimental data shows that embryos rehydrated directly in PB1 have better viability than embryos subjected to either of the step-wise rehydration procedures.

EXAMPLE 8

The direct transfer method of this invention can be used with embryos that have been developed from an in vitro matured oocyte. The immature oocytes are collected and cultured prior to fertilization. Various techniques have been known to those skilled in the art as described in Edwards, "Maturation In Vitro of Mouse, Sheep, Cow, Pig, Rhesus Monkey and Human Ovarian Oocytes," *Nature,* Vol. 208, pp. 349–351 (1965). More recently culture systems have been developed for various mammalian species including bovine oocytes. See e.g., Lu et al., "Pregnancy Established in Cattle by Transfer of Embryos Derived from In Vitro Fertilization of Oocytes Matured In Vitro," *Vet. Rec.,* Vol. 121, pp. 259–260 (1987). Any successful in vitro oocyte maturation process can be used to produce the embryos to be frozen and subsequently transferred according to the method of this invention.

Those skilled in the art upon reading the above detailed description of the present invention will appreciate that many modifications of the method described above can be made without departing from the spirit of the invention. All such modifications which fall within the scope of the appended claims are intended to be covered thereby.

EXAMPLE 9

The embryos used for the direct transfer technique of the present invention can be produced by gene transfer. Embryos produced are microinjected with gene constructs and subsequently cultured in an appropriate culture medium for development. Microinjection techniques for gene constructs are well-known to those skilled in the art. Appropriate culture media are discussed above in Example 7.

I claim:

1. A method for embryonic preservation for subsequent culture comprising the steps of
   (a) collecting embryos;

(b) placing the embryos in a cryoprotective container with ethylene glycol in a cell culture media of an isotonic salt solution;

(c) allowing the embryos to equilibrate in the cryoprotective solution;

(d) freezing the embryos for a desired time period;

(e) thawing the embryos; and (f) directly transferring the thawed embryos to a recipient animal.

2. A method of claim 1 wherein the embryos collected in step (a) are in the morula to hatched blastocyst stage.

3. A method of claim 1 wherein the embryos collected in step (a) are from artificially inseminated animals.

4. A method of claim 1 wherein the embryos collected in step (a) are produced by fertilization of in vitro matured oocytes.

5. A method of claim 1 wherein the embryos collected in step (a) are produced by in vitro fertilization of oocytes.

6. A method of claim 1 wherein the embryos collected step (a) are produced by in vitro culture of fertilized oocytes.

7. A method of claim 1 wherein the embryos collected in step (a) are produced by nuclear transfer.

8. A method of claim 1 wherein the embryos collected in step (a) are produced by embryo splitting.

9. A method of claim 1 wherein the isotonic salt solution in step (b) has an osmolality of 250 to 350 milliosmoles, a pH in the range of 6.8 to 7.6, a pH buffer, and is supplemented from a group consisting of protein sources, synthetic macromolecules, carbohydrates, amino acids and vitamins.

10. A method of claim 1 wherein the embryos in step (b) are placed with the cryoprotectant in containers suitable for cryopreservation that provide for direct transfer to recipient animals.

11. A method of claim 1 including the additional step of exposing the embryos to a solution containing about 0.05% to 0.5% trypsin in an isotonic salt solution prior to step (c), equilibration in the cryoprotective solution.

12. A method of claim 1 including the additional step of exposing the embryos to a pretreatment of other agents selected from the group consisting of proteolytic enzymes, detergents, and organic solvents.

13. A method of claim 1 including the additional step of combining the embryos with pieces of trophoblastic tissue from a different viable embryo prior to step (c).

14. A method of claim 1 wherein the embryos are allowed to equilibrate in step (c) for about 5 to about 40 minutes at a temperature in the range of from about 0° C. to 39° C.

15. A method of claim 1 wherein the freezing step (d) includes:

cooling the embryos in a controlled rate freezer by a procedure selected from the group consisting of (a) placing embryos directly into a freezing apparatus at a temperature slightly below the freezing point of the cryoprotective solution which is called the seeding temperature and (b) cooling the embryos at a controlled rate of about $-1°$ C./minute to the seeding temperature;

holding the embryos at the seeding temperature long enough to equilibrate the embryos at the seeding temperature; inducing ice nucleation by touching the cryoprotective container with a supercooled metal instrument;

continuing controlled rate cooling at a rate of about $-0.1°$ C./min. to $-1.0°$ C./min. to cool embryos to a range of about $-20°$ C. to about $-40°$ C.; and plunging the embryos into liquid nitrogen.

16. A method of claim 1 wherein the step (e) the embryos in the cryoprotective solution are thawed in a water bath at a temperature of about 30° C.

17. A method of claim 1 wherein the embryos collected in step (a) are matured after fertilization in an in vitro culture using a BRL co-culture.

18. A method of claim 1 wherein the embryos collected have exogenous DNA inserted by gene transfer.

19. A method for bovine embryonic preservation for subsequent culture comprising the steps of:

collecting Day 7 to 7½ bovine embryos in the late morula to expanded blastocyst stage;

placing the embryos in a cryoprotective solution of from about 1.0 M to about 2.0 M ethylene glycol and PB1 in plastic semen straws;

allowing the embryos to equilibrate for about 10 minutes at room temperature;

cooling he embryos in an alcohol bath freezer at $-7°$ C. for 2 minutes;

inducing ice nucleation by touching the straw with a supercooled metal instrument;

holding the embryos for 5 minutes at $-7°$ C.;

cooling at a controlled rate of $-0.5°$ C./minute to a final temperature of $-35°$ C.; holding at $-35°$ C. for 15 minutes;

plunging the straws into liquid nitrogen for long term storage;

thawing the embryos by placing the straws into a water bath of about 30° C. for 10 seconds; and transferring the thawed embryos directly to a recipient cow using an artificial insemination gun suitable for embryo transfer.

20. A method of claim 19 wherein the cryoprotective solution is comprised of 1.5 M ethylene glycol and PB1.

21. A method of claim 19 wherein the bovine embryos collected have been matured in an in vitro BRL co-culture system.

* * * * *